United States Patent [19]

Campbell et al.

[11] Patent Number: 4,743,560

[45] Date of Patent: * May 10, 1988

[54] SOLID PHASE ASSAY

[75] Inventors: Robert L. Campbell, Durham; Daniel B. Wagner, Raleigh; James P. O'Connell, Chapel Hill, all of N.C.

[73] Assignee: Becton Dickinson and Company, Franklin Lakes, N.J.

[*] Notice: The portion of the term of this patent subsequent to Oct. 27, 2004 has been disclaimed.

[21] Appl. No.: 593,411

[22] Filed: Mar. 26, 1984

[51] Int. Cl.$^4$ ............... G01N 33/533; G01N 33/543; G01N 33/544; G01N 33/548

[52] U.S. Cl. ................... 436/501; 436/510; 436/518; 436/528; 436/530; 436/800; 436/808; 436/815; 436/818; 436/829

[58] Field of Search ............... 436/501, 518, 519, 520, 436/523, 528, 532, 535, 829, 530, 534, 510, 800, 808, 815, 818; 435/7, 177, 180, 182, 810

[56] References Cited

U.S. PATENT DOCUMENTS

| | | | |
|---|---|---|---|
| 4,169,014 | 9/1979 | Goldberg | 435/182 |
| 4,483,929 | 11/1984 | Szoka | 436/534 |
| 4,496,658 | 1/1985 | Kondo et al. | 436/518 |
| 4,499,014 | 2/1985 | Estis | 435/272 |
| 4,552,812 | 11/1985 | Margel et al. | 436/501 |

FOREIGN PATENT DOCUMENTS

| | | | |
|---|---|---|---|
| 2523311 | 9/1983 | France. | |
| 80/01515 | 7/1980 | PCT Int'l Appl.. | |
| 85/01354 | 3/1985 | World Int. Prop. O. | 435/7 |
| 2099578 | 12/1982 | United Kingdom | 435/7 |

OTHER PUBLICATIONS

R. Hawkes et al, *Analytical Biochemistry*, 119, 142–147, 1982.

J. Huet et al, *Journ. Biol. Chem.*, 257, 2613–2618, 1982.

*Primary Examiner*—Sidney Marantz
*Assistant Examiner*—David A. Saunders
*Attorney, Agent, or Firm*—Elliot M. Olstein

[57] ABSTRACT

Solid phase assay for an analyte wherein binder is supported on a solid support, such as nitrocellulose, and the tracer is comprised of ligand labeled with a particulate label, such as a liposome, including a detectable marker which is not visible.

34 Claims, No Drawings

SOLID PHASE ASSAY

This invention relates to an assay for a ligand and to products used in such assay. More particularly, this invention relates to a solid phase assay.

Immunoassay methods, in general, are based on the competition between a specific analyte, the amount of which is to be determined in a sample, and a known amount of tracer, which is generally the analyte or appropriate analog thereof in labeled form, with the analyte and tracer competing for a limited number of available binding sites on a binder which is specific towards the analyte and tracer.

If the concentration of tracer and binder is fixed and the only variable is the level of analyte, it is possible to establish an assay system for measuring the unknown level of analyte by determining the amount of bound and/or free tracer in the system. The values determined in the assay are compared with the values given by a range of known amounts of the analyte treated in the same manner, and by such comparison, it is possible to determine the amount of analyte in the sample.

In one such procedure, the binder is supported on a solid support, whereby the bound and free components of the assay, after incubation, may be easily separated by separation of the sample and the solid support.

In general, the tracers used in such assays require either instrumentation and/or treatment of the tracer in order to determine the tracer in the bound and/or free portion of the assay as a measure of analyte. Thus, for example, in an assay in which an enzyme is used as the label or marker for the tracer, the enzyme must be developed with a suitable developer. When the label or marker is a fluorescent material, the tracer in the bound and/or free portion is determined by the use of appropriate instrumentation for determining fluorescence.

Although such assays are effective for determining analyte in a sample, there is always a need for increasing the sensitivity of the assay and for facilitating the overall assay procedure.

In accordance with one aspect of the present invention, there is provided a method and product for determining analyte wherein a binder for at least one of the analyte and tracer to be used in the assay is supported on a test area located on the surface of a solid support wherein the binder is supported on a test area of the solid support in a concentration of at least 1 $\mu g/cm^2$. The tracer used in the assay is a ligand labeled with a particulate label which contains a detectable marker which is not visible under assay conditions, and wherein the ligand is bound by either the binder or analyte.

More particularly, the solid support which is used in the assay is one which has a surface area (area/unit weight of material) such that the binder can be supported on the support in a concentration (weight/unit area) of at least 1 $\mu g/cm^2$.

The term "not visible" when referring to the detectable marker as used herein means that the marker cannot be seen without further treatment and/or without the use of instrumentation. thus, for example, a fluorescent marker requires excitation and an enzyme marker requires developing.

In accordance with still another aspect of the present invention, there is provided a method and product for determination analytes which are present in test samples in low concentrations wherein the analyte is detected on a test area located on the surface of a solid support by use of a tracer, wherein the solid support has a surface area such that the binder is supported on the test area in a concentration of at least 1 $\mu g/cm^2$. The tracer is a ligand labeled with a particulate label which includes a detectable marker which is not visible, and wherein the ligand is bound by either the binder or the analyte.

The solid support which is employed in the assay is generally a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such solid supports which are formed from cellulose esterified with nitric acid alone, or a mixture of nitric acid and another acid such as acetic acid, are often referred to as nitrocellulose paper.

Although nitrocellulose is a preferred material for producing the solid support, it is to be understood that other materials, having a surface area sufficient for supporting the binder in a concentration as hereinabove described may also be employed for producing such solid supports.

In general, the support which is used in the assay has a surface area such that it is capable of supporting binder in a concentration of at least 1 $\mu g/cm^2$, (most generally in a concentration of at least 10 $\mu g/cm^2$) and preferably at least 40 $\mu g/cm^2$.

In accordance with a particularly preferred embodiment, the pore size of the solid support is such that the tracer (ligand labeled with a particulate label), when bound to the binder or to the analyte bound to the binder, remains on the surface of the support. Thus, for example, particularly good results have been obtained with a nitrocellulose support having a pore size of from 0.2 to 0.45$\mu$.

Applicant has found that the sensitivity of the assay can be increased by increasing the concentration of binder on the support and, accordingly, supports having high surface areas (such as nitrocellulose) are particularly preferred in that the binder may be supported on such supports in a high concentration. It is to be understood, however, that the concentration of binder which is actually used is dependent in part on the binding affinity of the binder. Accordingly, the scope of the invention is not limited to a particular concentration of binder on the support.

Applicant has further found that it is possible to determine the detectable marker included in the particulate label, such as a sac, without releasing the marker from the sac.

The binder which is supported on the solid support, as hereinabove indicated, is either a binder for both the analyte and tracer, or a binder for only one of the analyte and tracer, with the type of binder which is employed being dependent upon the assay which is to be used for determining the analyte. Thus, for example, if the assay is a competition type of assay, then the binder supported on the solid support would be a binder for both the tracer and analyte, whereby both tracer and analyte would compete for a limited number of binding sites on the binder.

If the assay is a so-called "sandwich" type of assay, then the binder which is supported on the solid support is a binder for only the analyte. In such an assay, the tracer is a tracer which is specific for the analyte, whereby tracer is bound to the analyte which is bound to the supported binder.

If the assay is an inhibition type of assay, then the supported binder is specific for only the tracer, and the tracer is also specific for the analyte. In such an assay, the presence of analyte inhibits binding of tracer to the supported binder.

Thus, the tracer when bound to the solid support is either directly bound to the binder on the support or is bound to analyte which is bound to binder on the solid support.

The type of binder which is used in the assay is dependent upon the analyte to be assayed, as well as the specific assay procedure. As known in the art, the binder which is supported may be an antibody including monoclonal antibodies, an antigen, a protein specific for the material to be bound or a naturally occurring binder. Thus, for example, in a competitive type of assay for an antigen or hapten, the binder may be an antibody or a naturally occurring substance which is specific for the tracer and the antigen or hapten. If the assay is for an antibody, then the binder may be, for example, an antigen or an antibody which is specific for the antibody to be assayed. In a "sandwich" type of assay wherein the analyte is an antibody, the supported binder may be an antigen for the antibody, or a protein, such as protein A which selectively binds Fc fragments of certain antibodies. In a "sandwich" type of assay, if the analyte is an antigen (an antigen having more than one determinant site), then the binder may be an antibody or naturally occurring binder which is specific for the antigen to be assayed.

The selection of a suitable binder for support on the solid substrate is deemed to be within the scope of those skilled in the art from the teachings herein.

The ligand which is labeled for use as a tracer in the assay of the present invention is also dependent upon the analyte to be assayed, as well as the assay procedure. Thus, for example, if a competitive assay is employed for determining antigen or hapten, the ligand employed in producing the tracer would be either the analyte or appropriate analog thereof. (The term "appropriate analog" means that the analog of the analyte is bound by the binder for the analyte.)

If the assay is a "sandwich" type of assay for an antibody, then the ligand employed in producing the tracer would be a ligand which is specific for the analyte to be assayed, such as, for example, an antibody elicited in response to the antibody or antigen to be assayed. The selection of a suitable ligand for producing the tracer is deemed to be within the scope of those skilled in the art from the teachings herein.

As hereinabove indicated, in producing the tracer the ligand is labeled with a particulate label. A preferred particulate label is a sac, which includes a detectable marker which is not visible.

The sac which is used to label the ligand for producing a tracer may be any one of a wide variety of sacs, including but not limited to intact erythrocytes, erythrocyte ghosts, liposomes (single walled [sometimes called vesicles] or multilamellar), polymer microcapsules (for example, those made by coascervation, or interfacial polymerization), etc.

Erythrocyte ghosts are known in the art and are prepared by suspending erythrocyte cells in a solution of substantially lower osmolarity. The ghosts are "resealed" in an aqueous solution including the marker whereby the ghosts include the marker in the interior thereof. Such procedures are known in the art and the resealing solution of appropriate osmolarity generally includes, in addition to the marker, alkali and alkaline earth metal halides and a coenzyme; e.g., adenosine triphosphate. The preparation of ghosts, as sacs, is disclosed, for example, by D'Orazio et al, *Analytical Chemistry*, Vol. 49, No. 13, pages 2083–86 (Nov. 1977).

Polymer microcapsules are also produced by procedures known in the art except that the solution in which the microcapsules are formed also includes the marker whereby the interior of the polymer microcapsule includes the marker. The preparation of such microcapsules is disclosed for example in *Microencapsulation Processes and Applications*, edited by Jan E. Vandegger (Plenum Press 1974).

As known in the art, liposomes can be prepared from a wide variety of lipids, including phospholipids, glycolipids, steroids, relatively long chain alkyl esters ;e.g., alkyl phosphates, fatty acid esters; e.g., lecithin, fatty amines and the like. A mixture of fatty materials may be employed, such as a combination of neutral steroid, a charged amphiphile and a phospholipid. As illustrative examples of phospholipids, there may be mentioned lecithin, sphingomyelin, dipalmitoyl, lecithin, and the like. As representative steroids there may be mentioned cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g., dicetyl phosphate, stearyl amine, hexadecyl amine, dilauryl phosphate, and the like.

The liposome sacs are prepared in an aqueous solution including the marker whereby the sacs will include the marker in the interior thereof. The liposome sacs are easily prepared by vigorous agitation in the solution, followed by removal of marker from the exterior of the sac.

Further details with respect to the preparation of liposomes are set forth in U.S. Pat. No. 4,342,826 and PCT International Publication No. WO80/01515, both of which are hereby incorporated by reference.

As representative examples of detectable markers which may be included in the sac, there may be mentioned: fluorescent materials, radioisotopes; enzymes, spin labels, chemiluminescent materials, etc.

The ligand may be labeled with the particulate label so as to produce a tracer for use in the invention by procedures generally known in the art, with the procedures which is used being dependent upon the ligand and the particulate label which is employed. Such techniques include adsorption, covalent coupling, derivatization, coactivation, the the like. In producing a tracer wherein the ligand is labeled with a sac, the sac may be produced from a component which has been derivatized with a ligand, whereby the sac, when produced, is sensitized with the ligand. In another procedure, the sac including the marker may be initially formed, followed by sensitizing the sac with ligand by procedures known in the art.

Thus, the tracer is comprised of a ligand and a particulate label (solid or solid-like, as opposed to non-solid labels, such as radioisotopes, enzymes and various fluorescent materials), and the particulate label includes the detectable marker.

The solid substrate employed in the assay is preferably in sheet form, with the substrate, in sheet form, generally being in the form of a card, a test strip or dipstick, etc. It is to be understood, however, that other forms are also within the spirit and scope of the invention.

The binder is supported on the solid substrate by applying a solution of the binder to a defined area of the test substrate; such as, for example, in the form of a spot, which can be located in a marked area; e.g., square or circle, on the substrate. Particularly good results have been obtained when the binder is applied to the test area as a spot having a diameter of from 3 to 5 mm. The concentration of the binder placed in the defined test area will vary depending upon the assay to be performed; however, the binder is generally present in a concentration of at least 1 $\mu g/cm^2$ (most generally at least 10 $\mu g/cm^2$), and preferably at least 40 $\mu g/cm^2$. Similarly, the test substrate may contain more than one test area, and each test area may include the same binder, with different affinities and/or in different concentrations, and/or with the same concentration and/or affinity, or the various test areas may include different binders, in which case, the assay may be employed for determining more than one analyte. Although the binder may be appropriately applied to the test substrate for support thereon by adsorption, it is also to be understood that in some cases it may be necessary or desirable to provide for covalent coupling of the binder to the test substrate.

After application of the binder to one or more test areas on the substrate, the residual binding capacity of the test substrate is saturated or blocked by treatment of the test substrate with one or more types of proteins which do not specifically bind the materials to be employed in the assay. Thus, for example, the residual binding capacity of the substrate may be blocked so as to prevent non-specific binding by the use of bovine serum albumin. The techniques for preventing non-specific binding are generally known in the art, and such techniques are also generally applicable to preventing non-specific binding in the assay of the present invention.

The binder supported on the substrate, as hereinabove described, may be employed in an assay for an analyte employing an appropriate tracer as hereinabove described. Thus, for example, in one assay technique useful in determining a hapten or antigen, an antibody supported on an appropriate test area of the solid substrate in a concentration as hereinabove described; in particular, a support formed from nitrocellulose, is contacted and incubated for an appropriate time with a sample containing or suspected of containing analyte. Subsequently, the substrate is washed with buffer, and contacted with tracer, which is preferably the analyte or appropriate analog thereof coupled to a particulate label, preferably a liposome containing a detectable marker which is not visible. The amount of tracer which becomes bound to the supported antibody is inversely proportional to the amount of analyte in the sample. Unbound tracer is rinsed from the substrate, and the presence and/or amount of tracer which remains bound to the substrate may be determined as a measure of the presence and/or amount of analyte present in the sample.

In accordance with the present invention, it is possible to determine the presence and/or concentration of tracer on the test substrate without lysing of the liposome. Thus, unlike prior art procedures wherein the detectable marker within the liposome is determined after lysis of the liposome, by proceeding in accordance with the present invention it is possible to determine the tracer on a solid support, without lysis of the liposome.

As an alternative to the above procedure, instead of sequentially adding sample and tracer, the substrate containing the supported antibody may be simultaneously contacted with the analyte to be determined and tracer.

In another type of assay, the "sandwich" technique is employed for determining analyte. In such a technique, the binder supported on a solid support in an appropriate concentration, as hereinabove described, is initially contacted with analyte; for example, antigen. Subsequently, the antigen bound to the binder on the solid support is contacted with tracer, which is, for example, antibody to the analyte labeled with a particulate label, preferably a liposome containing a detectable marker. The amount of tracer which is bound to the binder on the solid support through the analyte is directly proportional to the amount of analyte in the sample, and the presence and/or amount of analyte present in the sample may be determined from the presence and/or amount of tracer which becomes bound to the support through the analyte. As hereinabove described, in accordance with the present invention, it is possible to determine the amount of tracer and/or the presence or tracer by use of a sac, including a detectable marker which is not visible, without lysing of the sac.

Assays for various analytes may be readily accomplished in accordance with the present invention by coordinating the amount of binder placed on the test area with other assay parameters so that the analyte can be determined in the range of interest.

By use of a tracer as hereinabove described; e.g., ligand labeled with liposome containing a detectable marker which is not visible, and a nitrocellulose support on which a binder is supported in a test area, and by coordinating the affinity of the binder and/or the dilution, with other assay parameters, it is possible to provide a quantitative assay by use of a standard curve generated by procedures known in the art.

The present invention may be employed for determining analytes which are generally present in a sample to be assayed in low concentrations. Thus, for example, the present invention may be employed as an assay with sensitivities for analyte concentrations of $10^{-9}$ g/ml and less. Thus, the assay of the present invention may be employed as an assay for the analytes which are known to be present in samples of interest in very low concentrations (for example, hCG (human chorionic gonadotropin), digoxin, leutinizing hormone).

In accordance with another aspect of the invention, there is provided a reagent kit or package for accomplishing an assay for an analyte which includes: (a) a solid support having at least one test area, in which a binder for at least one of the analyte and tracer to be used in the assay is supported in a concentration of at least 1 $\mu g/cm^2$ (most generally at least 10 $\mu g/cm^2$ and preferably at least 40 $\mu g/cm^2$; (b) a tracer which is a ligand labeled with a particulate label, including a detectable marker which is not visible, said tracer being bound by one of the analyte and binder. In accordance with a preferred embodiment, the solid support is in sheet form and is prepared from nitrocellulose. Although the support is preferably formed of nitrocellulose, other materials having a surface area sufficient for supporting the binder in requisite concentrations may be employed. As hereinabove indicated, the support may include more than one test area, and such plurality of test areas may include the same binder in different concentrations; the same binder having different affinities; or different binders. In accordance with a preferred embodiment, the tracer is labeled with a sac (preferably a liposome) which includes a detectable marker which not visible.

The kit or package may include other components such as standards of the analyte (analyte samples having known concentrations of the analyte), known buffers and the like.

The present invention is applicable to procedures and products for determining a wide variety of analytes. As representative examples of types of analytes, there may be mentioned: drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hCG; insulin; theophylline; leutinizing hormone; organisms causing or associated with various disease states, such as streptococcus pyogenes (group A), Herpes Simplex I and II, cyto-megalovirus, chlamydia, etc.

The analyte may be determined in various samples, including for example, body fluids, such as urine, serum, etc. In some cases, it may be possible to detect analyte in whole blood.

The assay may be qualitative (presence or absence of certain level of analyte) or quantitative or semi-quantitative. The preparation of suitable standards and/or standard curves is deemed to be within the scope of those skilled in the art from the teachings herein.

As hereinbefore indicated, the tracer may be determined on the solid support with or without lysis of the sac.

Thus, for example, in the case where the detectable marker is a fluorescent material, fluorescence can be determined without destruction of the sac by the use, for example, of an appropriate ultraviolet lamp or more complex instrumentation such as a reflectance fluorimeter, fluorescence scanning densitometer, etc.

A radioactive marker may be determined without destruction of the sac by the use of an appropriate counter.

Alternatively, the sac may be lysed so as to determine the marker. Thus, for example, in the case of a fluorescent marker, the sac can be destroyed and fluorescence determined on the strip. In another embodiment, when using a nitrocellulose strip, the sac may be destroyed and the released fluorescent marker may be separated from the test strip by use of an appropriate solvent for the fluorescent material; e.g., by passing the solvent containing the fluorescent material through the test strip.

In another embodiment, in the case where the marker is an enzyme or luminescent material (chemiluminescent or bioluminescent), the permeability of the liposome membrane may be altered to permit an appropriate developer to enter the liposome so as to generate an appropriate signal, without destroying the sac. Thus, for example, in the case where the marker is an enzyme encapsulated in the liposome, a color producing reaction may be effected by changing the permeability of the liposome membrane (change of ionic strength of solution; or pH; etc.) so that an appropriate developer may enter the sac to generate color.

The tracer used in the present invention may include a particulate label other than a sac; for example, the particulate label may be formed from a polymer particle in which the non-visible detectable marker is physically trapped or bonded. Thus, for example, a polystyrene particle including a fluorescent material so as to provide a fluorescent particle may be employed as a particulate label in accordance with the present invention. Similarly, the polymer particle may include a radioactive material.

The present invention is particularly advantageous in that very sensitive assays can be performed with sufficient signal so that it is not necessary to destroy the sac; i.e., the encapsulated marker does not have to be released before results are determined, thereby removing a step and simplifying the assay. In addition, the assay can be rapidly performed.

Because of the overall simplicity of the assay to the end user, the assay can be readily performed by untrained persons. The solid phase, once prepared, should be stable for long periods of time. Minor errors in sample volume added or in volume of tracer added do not significantly affect the assay results. The assay described herein is sufficiently simple and reliable even for use in the home, and in this case, has sufficient sensitivity to detect a wide variety of analytes not commonly available in a simple test format.

Thus, for example, as a result of its sensitivity, an hCG assay performed in accordance with the present invention can detect pregnancy in its early stages. Moreover, such a test can be easily adopted to home use as a result of its simplicity.

Particularly good results (high sensitivity) are obtained when the particulate label is a liposome; however, the scope of the invention is not limited to liposomes.

The invention will be further described with respect to the following examples; however, the scope of the invention is not to be limited thereby:

EXAMPLE I

Liposome Preparation

1. To a 100 ml round-bottom rotoevaporator flask, add the following:
   a. 48 mg cholesterol, Sigma #CH-S
   b. 104 mg distearoyl phosphatidyl choline (DSPC), Avanti Polar Lipids #850365 (20 mg/ml in $CHCl_3$)
   c. 3.75 mg crosslink agent (distearoyl phosphatidyl ethanolamine-(p-maleimidophenyl) butyrate (DSPE-MPB) prepared in-house, 2 mg/ml in $CHCl_3$ as described in Example IA.)
   d. 6.0 ml isopropyl ether, Fisher #E-141
   e. 1.0 ml methanol, Aldrich #15,490-3
2. Swirl to mix.
3. Add 5.0 ml 0.01 M Sulforhodamine B, Eastman #14321, prepared in 0.1 M sodium acetate/0.1 M NaCl, pH 4.5 buffer.
4. Swirl to mix.
5. Flush vessel with $N_2$.
6. Sonicate in room temperature, water bath sonicator for 10 min in order to emulsify.
7. Place on rotoevaporator with the following settings: Water bath temperature = 44° C. Rotation speed = 4 rpm
8. Slowly increase vacuum until foaming ceases (approximately 30–40 min).

9. Reduce pressure and allow liposomes to anneal at 44° C. for 30 min.
10. Add 10 ml of warm (50°-52° C.) 0.1 molar sulforhodamine B to vessel and mix.
11. Extrude the warm liposome preparation through a 0.4 micron then a 0.2 micron Biorad Unipore polycarbonate membrane (Biorad #313-0059 and #313-5059, respectively).
12. Dilute liposomes to a total volume of approximately 80 ml in a 90 ml ultracentrifuge tube using sodium acetate/saline buffer, pH 4.5.
13. Centrifuge at 75,000 Xg for 30 min.
14. Resuspend pelleted liposomes to 80 ml with sodium acetate/saline buffer, pH 4.5.
15. Repeat #13 and #14, then #13 again.
16. Resuspend pelleted liposomes in 10 ml Tris buffer, pH 8.0 (50 mM Tris, 100 mM NaCl , 1 mM EDTA, 310 mOs/kg).
17. Hold at 4° C. until protein reaction.

EXAMPLE IA

Preparation of Distearoylphosphatidylethanolaminemaleimidophenylbutyrate used in Example I Distearoylphosphatidylethanolamine (119.2 mg, 0.1593 mmol, Avanti Polar Lipid) was suspended in 30 ml of chloroform and heated to reflux under a nitrogen atmosphere until all solid had dissolved. The solution was allowed to cool to room temperature followed by the addition of triethylamine (22.2 ul, 0.1593 mmol, Aldrich) and succinimidyl-4-(p-maleimidophenyl) butyrate (79.45 mg, 0.2230 mmol, Pierce). The reaction mixture was allowed to stir overnight at room temperature under a nitrogen atmosphere. The mixture was concentrated under reduced pressure to yield a pale yellow waxy solid (270.7 mg) that appeared as one major spot and several minor spots upon TLC analysis (silica, 65:25:4 $CH_2Cl_2:CH_3OH:H_2O$). The spot was visualized with UV light and Molybdenum Blue Spray Reagent (Sigma), $R_f$ 0.5

The crude product was chromatographed on four silica gel, preparative, thick-layer plates (E. Merck, 2.0 mm) developing with 65:25:4 $CH_2Cl_2:CH_3OH:H_2O$. The upper band of the two Molybdenum Blue active bands was isolated and the product extracted with 50% $CH_2CL_2:C_2H_5OH$. Evaporation of the solvent afforded the product as a white solid (65.75 mg).

IR (Neat) : 2910(s), 2845(s), 1734(s), 1715(s), 1510(m), 1460(m), 1390(m), 1370 (mw), 1242(m), 1230(m), 1100(m), 1060(m), 905(m), 820(m), 685 cm$^{-1}$(m).

The liposomes prepared in this manner include rhodamine dye and may be sensitized with a ligand by procedures known in the art to produce a tracer for use in the present invention.

The following Example II illustrates the preparation of tracer by sensitizing the liposome with an antibody.

Sensitizing Liposome (Example I) with Antibody to Produce Tracer

EXAMPLE II

1. To 8 mg protein A purified antibody, add 0.4 ml 1 M dithiothreitol in sodium acetate/saline buffer, pH 4.5.
2. Vortex and let react 30 min at room temperature in the dark.
3. Remove dithiothreitol by passing the reaction volume over a Sephadex G-25 medium column equilibrated with Tris ph 8.0 buffer (50 mM Tris, 100 mM saline, 1 mM EDTA, 310 mOs/kg).
4. Monitor the O.D. 280 and pool void volume fractions.
5. Mix this solution with the 10 ml of freshly prepared liposomes.
6. Flush with $N_2$ and seal.
7. React overnight at room temperature.
8. Wash twice, by centrifugation, these protein-labeled liposomes using the standard Tris buffer.
9. After last wash, resuspend pellet in 40 ml Tris.
10. Store at 4° C.

EXAMPLE III

Nitrocellulose Disc Immunoassay for HCG (Pregnancy Test)

Reagents
1. Adsorption Buffer 5: BD, Catalog #614335
2. HCG antibody to the alpha-chain of hcG
3. Nitrocellulose Paper: Schliecher & Schuill, ME 25, 0.45 um porosity
4. Bovine Serum Albumin: Sigma, Catalog #A-7906
5. Urine Controls: BDI, Catalog #255815
6. Tracer: Liposome prepared by method of Example I and sensitized with antibody to the B chain of hcG by the method of Example II.

Procedure:
1. Cut 1 cm disc of nitrocellulose paper.
2. Pipet 3 ul of 1:50 dilution of hCG antibody (dilution made in AB5) to the center of disc.
3. Allow to dry at room temperature 15 minutes.
4. Pipet 300 ul of 5% BSA in AB5 (filtered through 0.45 micron filter prior to use) to each disc.
5. Incubate disc 1 hour at 37° C.
6. Decant liquid.
7. Pipet 200 ul of urine control or urine.
8. Incubate 1 hour at room temperature.
9. Decant control or urine.
10. Wash disc twice with 1.5 ml AB5.
11. Pipet 300 ul of 1:12 dilution of tracer (dilution made in AB5) to each disc (stock liposomes contain about 1$\mu$ mole lipid/ml)
12. Incubate 1 hour at room temperature.
13. Decant tracer.
14. Wash twice with 1.5 ml AB5.
15. Visible spot when viewed under UV light is positive for pregnancy.

EXAMPLE IV

Preparation of Distearoylphosphatidylethanolamine-Digoxigenin

Distearoylphosphatidylethanolamine (400.0 mg, 0.5346 mmol, Avanti Polar Lipid) was suspended in 50 ml of $CHCl_3:CH_3OH$ (9:1) and heated to reflux under a nitrogen atmosphere until all solid had dissolved. The solution was allowed to cool followed by the additionof 3-ketodigoxigenin (207.7 mg, 0.5346 mmol) and 2.0 g of 4A sieves (Sigma). The reaction mixture was allowed to stir at 60° C. for 3 hr. under a nitrogen atmosphere at which time sodium cyanoborohydride (36.95 mg, 0.5881 mmol, Sigma) was added. The mixture was then allowed to stir at room temperature overnight. The reaction was filtered and concentrated under reduced pressure to yield a white foam (579.6 mg) that appeared as one major spot and several minor spots under TLC analysis (silica, 20% $CH_3OH:CH_2Cl_2$). The spot was visualized by Phosphomolybdic Acid Spray Reagent (Sigma), R$_f$ 0.3.

The crude product was purified by low pressure column chromatography (silica gel, 10% CH$_3$OH-CH$_2$Cl$_2$) to yield the product as a white solid (185.3 mg). The product was detected by a variable wavelength UV detector set at 230 nm.

EXAMPLE V

Preparation of Liposome Containing Rhodamine Dye Sensitized with Digoxigenin (Tracer)

Phosphatidyl choline, dipalmitoyl (dppc), cholesterol (chol), phosphatidyl ethanolamine, disteraroyl-digoxigenin (dspe-dig) (Example V), and phosphatidyl glycerol, dipalmitoyl (dppG) are dissolved in chloroform/methanol (20:1) in the ratio of 50 mole % chol, 40 mole % dppc, 10 mole % dppg and a trace amount (e.g., 200 ug) of dspe-dig is added. The lipids are dried on the inside of a round bottom flask under reduced pressure on a rotary evaporator, and subsequently placed on a lyophilizer overnight to remove all traces of residual solvent. A solution of 0.01M sulforhodamine B in water is added to the flask (10 ml), and the flask is shaken vigorously or, if desired, sonicated briefly. This operation is conducted at 60° C. The liposomes form spontaneously under this condition as is known in the art, and contain approximately 0.1M rhodamine dye encapsulated. Detectable digoxigenin is exposed on the surface of the liposomes. The liposomes are washed several times in a buffer solution of the same osmolarity as the encapsulated dye (about 310 mosm/Kg) to prevent osmotic lysis. The preparation is filtered through a 0.4 or 0.2u filter to remove the larger liposomes. The liposomes are diluted in buffer solution so as to contain 1u mole of phospholipid per ml of buffer solution.

Although the tracer may be determined without lysis or destruction of the sac containing the marker, it is to be understood that the scope of the invention and claims is not limited to such a determination in that, as should be apparent, a user of the assay could elect to destroy the sac before making the determination.

Numerous modifications and variations of the present invention are possible in light of the above teachings and, therefore, within the scope of the claims the invention may be practiced otherwise than as particularly described.

What is claimed is:

1. A process for assaying for an analyte, comprising: contacting a binder supported on a test area of a solid support with analyte and a tracer, said binder being a specific binder for at least the analyte, said tracer being comprised of a ligand labeled with a liposome, said liposome including a detectable marker which is not visible, said ligand being bound to one of the binder on the support or the analyte bound to the binder on the support, said test area being formed of a material having a surface area for supporting the binder and said binder being supported in the test area in a concentration of at least 1 ug/cm and at which tracer may be determined without lysis of the liposome; and
determining the tracer bound in said test area as a measure of analyte in a sample.

2. The process of claim 1 wherein analyte and tracer are sequentially contacted with the binder on the solid support.

3. The process of claim 1 wherein the analyte and tracer are simultaneously contacted with binder on the solid support.

4. The process of claim 1 wherein the analyte is digoxin.

5. The process of claim 1 wherein the analyte is (hCG) human chorionic gonadotropin.

6. The process of claim 1 wherein the tracer is determined without lysis of the liposome.

7. The process of claim 1 wherein the solid support is in sheet form.

8. The process of claim 1 wherein the binder is an antibody.

9. The process of claim 8 wherein the tracer is a labeled form of the analyte.

10. The process of claim 8 wherein the tracer is a labeled form of an antibody for the analyte.

11. The process of claim 1 wherein the assay is for human chorionic gonadotropin the binder is antibody to human chorionic gonadotropin and said tracer is comprised of antibody to human chorionic gonadotropin labeled with a (sac) liposome containing a fluorescent material as said detectable marker.

12. The process of claim 11 wherein the test area is formed of nitrocellulose.

13. The process of claim 1 wherein the assay is for digoxin, said binder is antibody to digoxin and the tracer is comprised of an analogue of digoxin (bound by said antibody) labeled with a sac containing a fluorescent material as said detectable marker(.), said analogue being bound by said antibody.

14. The process of claim 13 wherein the test area is formed of nitrocellulose.

15. A process for assaying for an analyte, comprising:
contacting a binder supported on a test area of a solid support with analyte and a tracer, said binder being a binder specific for at least the analyte, said tracer being comprised of a ligand labled with a liposome including a detectable marker which is not visible, said ligand being bound to one of the binder on the support or the analyte bound to the binder on the support, said test area being formed of nitrocellulose, said binder being supported in the test area in a concentration of at least 1 ug/cm and at which tracer may be determined without lysis of the liposome; and
determining the tracer bound in said test area as a measure of analyte in a sample.

16. The process of claim 15 wherein the tracer in said test area is determined without lysis of the liposome.

17. The process of claim 16 wherein the analyte is (hCG) human chorionic gonadotropin.

18. The process of claim 16 wherein the analyte is digoxin.

19. The process of claim 16 wherein the analyte is in a sample in a concentration of no greater than $10^{-9}$ gm/ml.

20. The process of claim 15 wherein the analyte is in a sample in a concentration of no greater than $10^{-9}$ gm/ml.

21. The process of claim 15 wherein the solid support is in sheet form.

22. The process of claim 15 wherein the support contains a plurality of said test areas.

23. The process of claim 15 wherein the binder is supported in a concentration of at least 40 $\mu$g/cm$^2$.

24. The process of claim 23 wherein the binder is in the test area as a spot having a diameter of from 3 to 5 mm.

25. A reagent kit for determining an analyte comprising:

a solid support including a binder on a test area of a solid support; and a tracer, said binder being a binder specific for at least the analyte, said tracer being comprised of a ligand labeled with a liposome containing a detectable marker which is not visible, said ligand being bound to one of the binder on the support or the analyte bound to the binder on the support during an assay, said test area being formed of a material having a surface area supporting the binder and the binder being supported in a concentration of at least 1 ug/cm and at which tracer may be determined without lysis of the liposome.

26. The kit of claim 25 wherein the (binder) test area is formed of nitrocellulose.

27. The kit of claim 26 wherein the label of the tracer is a liposome including a fluorescent material as said marker.

28. The kit of claim 26 wherein the binder is an antibody.

29. The kit of claim 28 wherein the analyte is digoxin, the binder is antibody to digoxin and the ligand of the tracer is an analogue of digoxin.

30. The kit of claim 28 wherein the analyte is (hCG) human chorionic gonadotropin.

31. The kit of claim 30 wherein the binder is antibody to (hCG) human chorionic gonadotropin and the ligand of the tracer is antibody to (hCG) human chorionic gonadotropin.

32. A process for assaying for an analyte, comprising:

contacting a binder supported on a test area of a solid support with analyte and a tracer, said binder being a specific binder for at least the analyte, said tracer being comprised of a ligand labeled with a lipsome, said liposome including a detectable marker which is not visible, said test area being formed of a material having a surface area for supporting the binder and the binder being supported in the test area in a concentration of at least 1 ug/cm and at which tracer may be determined without lysis of the liposome; and determining the tracer bound in said test area as a measure of analyte in a sample.

33. The process of claim 32 wherein the test area is formed of nitrocellulose.

34. The process of claim 32, wherein the tracer is determined without lysis of the liposome.

* * * * *